United States Patent [19]
Graves et al.

[11] Patent Number: 4,822,845
[45] Date of Patent: Apr. 18, 1989

[54] RUBBER COMPOSITIONS MODIFIED WITH HETEROCYCLIC DI-N-OXIDES

[75] Inventors: Daniel F. Graves, Clinton, Ohio; Hans-Wilhelm Engels, Kerpen, Fed. Rep. of Germany

[73] Assignee: The Firestone Tire & Rubber & Company, Akron, Ohio

[21] Appl. No.: 37,486

[22] Filed: Apr. 13, 1987

[51] Int. Cl.$^4$ .......................... C08K 3/04; C08K 5/34; C08C 4/00

[52] U.S. Cl. .................................. 524/519; 152/548; 152/564; 524/92; 524/496; 524/523; 524/525; 524/526; 524/552; 524/555; 524/560; 524/565; 524/566; 524/573

[58] Field of Search ................... 152/564, 374 R, 548; 524/566, 575, 92, 571, 496, 565, 523, 519, 525–526, 552, 555, 573

[56] References Cited

U.S. PATENT DOCUMENTS

| | | | |
|---|---|---|---|
| 2,367,827 | 1/1945 | Smith | 260/788 |
| 4,259,218 | 3/1981 | Haws | 260/5 |
| 4,309,318 | 1/1982 | Ahagon et al. | 260/5 |
| 4,557,306 | 12/1985 | Graves | 524/92 |
| 4,570,690 | 2/1986 | Graves | 524/92 |

FOREIGN PATENT DOCUMENTS

0159469 1/1985 European Pat. Off.
0156755 2/1985 European Pat. Off.
2010850 11/1978 United Kingdom.

(List continued on next page.)

OTHER PUBLICATIONS

M. J. Haddadin et al, Tetrahedron, 32, 719 (1976).
K. Ley and F. SEng, Synthesis, 415–422 (1975).

(List continued on next page.)

Primary Examiner—Herbert J. Lilling
Attorney, Agent, or Firm—Renner, Otto, Boisselle & Sklar

[57] ABSTRACT

It now has been found that uncured rubber composition comprising rubbers having an unsaturated carbon chain and at least one carbon black can be improved by including therein, a minor property-improving amount of at least one aromatic heterocyclic di-N-oxide compound of the partial formula

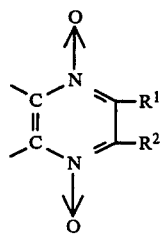

(I)

wherein the depicted carbon atoms are part of an optionally substituted aromatic ring, and $R^1$ and $R^2$ are each independently hydrogen, hydrocarbyl, halohydrocarbyl, hydrocarbyloxy, hydrocarbyl sulfonyl, hydrocarbyl thio, hydrocarbylsulfoxidyl, halogen, amino,

—CN

—OH

—CHO

—CH(O hydrocarbyl)$_2$

—C(O)R$^3$

—C(O)OR$^3$

—C(N—OH)R$^3$

—C(O)NR$^3$R$^6$

—CH=N—NH—C(O)OR$^3$

—CH$_2$OC(O)CH$_3$

—R$^4$YR$^3$

—C(O)NHR$^4$OH

—C(NH)NR$^7$R$^8$, or

—C(O)NHN(R$^3$)$_2$ wherein each $R^3$ is independently hydrogen or a hydrocarbyl group, $R^4$ is a divalent hydrocarbyl group, $R^6$ is hydrogen, hydrocarbyl, —R$^4$OR$^3$, or —R$^4$COOR$^3$; $R^7$ is hydrogen or a hydrocarbyl group; $R^8$ is hydrogen or a hydrocarbyl, an amino, or a hydroxyl group; $R^7$ and $R^8$ may be hydrocarbyl groups joined together to form a ring including the nitrogen atom, and Y is O, divalent S, —NH—, —S(O)— or —S(O)$_2$ or $R^1$ and $R^2$ may be joined together to form further ring systems which may be saturated or unsaturated, and further substituted or unsubstituted. When vulcanizates are prepared from such uncured rubber compositions, particularly when the carbon black used therein has an average surface area of at least about 20 m$^2$/g, the vulcanizates exhibit reduced low strain hysteresis and exhibit no significant undesirable odor.

In another aspect of the invention, a filled vulcanizate made by vulcanizing uncured compositions of the type described above and containing a filler, particularly carbon black, is improved in filler interaction, hysteresis, modulus, compression set and resiliency. Rubber articles and portions thereof made from such vulcanizates such as tires, hoses, belts, springs, treads, sidewalls, and the like can be made utilizing the improved filled vulcanizates of the invention.

29 Claims, No Drawings

FOREIGN PATENT DOCUMENTS 2,922,938 12/1980 Fed. Rep. of Germany.
0,069,054 1/1983 European Pat. Off.
8,404,822 12/1984 World Intellectual Property Org.
6,057,303 4/1985 Japan.

OTHER PUBLICATIONS

M. J. Haddadin et al, Heterocycles 4, 767 (1976).

M. J. Haddadin, and G. H. Issidorides, J. Org. Chem. 37, 589 (1972).

J. W. McFarland, J. Org. Chem. 36, 1842 (1971).

E. Abushanab J. Org. Chem. 35, 4279 (1970).

A. Gasco and A. J. Boulton, Advances in Heterocyclic Chem., vol. 29, 306 Academic Press, 1981.

Applied Optics, Vol. 22, No. 12, June 1983, New York, pp. 1918-1922; J. Bures et al.: "Analyse d un copleur bidirectionnel a fibres optiques monomodes fusionnes".

RUBBER COMPOSITIONS MODIFIED WITH HETEROCYCLIC DI-N-OXIDES

TECHNICAL FIELD OF THE INVENTION

This invention relates to uncured rubber compositions, filled vulcanizates and rubber articles such as tires, treads, hoses, belts, etc. made therefrom. More particularly, the invention relates to rubber compositions exhibiting improved properties (e.g., reduced hysteresis) and containing one or more heterocyclic di-N-oxides. The invention also relates to articles made from such vulcanizates such as tires, tire treads, etc. and methods of improving the rolling loss and running temperature of such tires.

BACKGROUND OF THE INVENTION

It is known that rubber compositions generally are combined or "compounded" with various other materials before being cured and/or put into one. Some of these added materials improve the properties of the end product in service while others improve processing properties of the uncured compositions. In some instances, both effects may be achieved. It is also known that the various chemicals, pigments and other materials so used, both organic and inorganic, can interact in various ways to produce desirable or deleterious effects. For further discussions of rubber processing and materials used therein, see, for example, *Encyclopedia of Polymer Science and Technology*, Second Edition, published by John Wiley and Sons, New York (1970), particularly Vol. 12, page 280 and *The Vanderbilt Rubber Handbook*, R. T. Vanderbilt Company, Norwalk, Conn., 06855 (1968), particularly Sections 6, 7, 8, 9 and 11.

Vulcanizing agents, plasticizers, extenders, accelerators, fillers, pigments, etc. generally are incorporated into vulcanizable rubber compositions so that the rubber can be cured or vulcanized in a mold to form useful articles. It often is necessary to include processing aids in rubber compounds prior to molding and curing. These aids are primarily intended to improve the mixing of the ingredients of the rubber compound, the processability of the rubber, the mold or mill release properties of the rubber, tack and green strength without seriously adversely affecting the properties of the cured rubber.

Vulcanizing or curing agents used in vulcanizable rubbers generally are sulfur or sulfur-containing compounds or peroxide compositions. The rate of the vulcanization reaction generally is slow with many rubber materials unless an accelerator is incorporated into the vulcanizable mixture. A number of materials have been suggested and utilized for their accelerating effect. Such materials include metal oxides, for example, lead oxide, calcium oxide and magnesium oxide. Organic accelerators have found wide use in today's technology, and many of these are derivatives of aniline. A larger portion of the organic vulcanization accelerators which are in current use are derivatives of 2-mercaptobenzothiazole (MBT). One group of MBT derivatives which has found wide acceptance includes the N-derivatives of 2-benzothiazole sulfenamide. A number of such derivatives and their use as accelerators of vulcanization are described and discussed in Vol. 20 of the *Encyclopedia of Chemical Technology*, Kirk-Othmer editors, Second Edition, 1983, pp. 337–363. See also U.S. Pat. No. 2,367,827.

In order to minimize or eliminate premature curing of the rubber formulation (scorching), the vulcanizing agents and accelerators are added to the formulation just prior to the curing step. The other normally used rubber formulation additives are mixed with the base rubber compositions in, for example, a masterbatch operation, prior to contact with the sulfur and accelerator.

Carbon blacks are used in rubber formulations and vary widely as to their characteristics and combinations of characteristics. In rubber formulations, carbon black is used as a reinforcing filler. Many carbon blacks of the channel and furnace types with varying characteristics have been utilized because they impart varying desirable characteristics to the rubber. The formation of a secondary network structure in rubber stocks containing reinforcing carbon blacks leads to high hysteresis at low deformations. Various additives have been suggested in the art to reduce the hysteresis of such rubber stocks. Hysteresis is defined in the *Dictionary of Rubber Technology*, A. S. Craig, Philosophical Library Inc., New York, p. 80, as the difference between the energy input and energy output when rubber is deformed. The loss in energy is consumed in internal friction and results in heat buildup. Thus tires made of rubber exhibiting high hysteresis are characterized by high running temperatures.

As mentioned, the present invention relates to tires having low rolling loss. Since the tread portion of a tire is adapted to be ground contacting and occupies a considerable portion of the tire thereof, it is advantageous to use a tread composition which will produce a tread having desirable properties. Rubber compositions which will produce tires having a small hysteresis loss due to deformation of the tires when they are rolled have been used in the industry in attempts to obtain tires having decreased rolling resistance. Conventional tread compositions normally are composed of materials which tend to increase hysteresis loss in the resulting treads.

One of the difficulties of producing treads having decreased hysteresis loss is the potential resulting loss of other desirable properties such as braking performance wet and dry traction, and wear resistance. Thus, it is desirable to develop rubber formulations useful in making the treads of tires which reduce the hysteresis loss of the treads without impairing braking performance, traction, wear resistance and other desirable properties.

British Patent Application GB No. 2010850A describes the use of certain heterocyclic di-N-oxides as cross-linking agents for unsaturated polymers, especially rubbers. In general, the heterocyclic di-N-oxide compounds are defined as compounds whose structure comprises a 6-membered hetero-aromatic ring consisting of four carbon atoms and two nitrogen atoms in the 1,4-position of the ring, both nitrogen atoms being oxidized to N-oxide groups. A preferred example of such compounds listed in the British patent is represented as

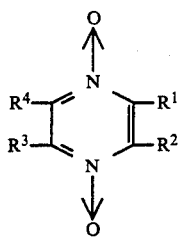

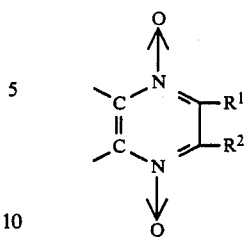

(I)

wherein the R groups $R^1$, $R^2$, $R^3$ and $R^4$ may be hydrogen, alkyl, aryl, alkoxy, aryloxy, alkaryl, aralkyl, acyl, alkylsulfonyl, arylsulfonyl, halogen or nitro. Two or more of the $R^1$-$R^4$ groups may be linked together to form further ring systems and any of the groups or ring systems may be further substituted. In a specially preferred class of compounds described in the British patent as the above-identified compound has the two carbon atoms in the two and three-position of the ring fused to an aromatic ring. The patentees indicate that the cross-linked polymers obtained by the process of the invention are of higher molecular weight and possess better tensile properties than before cross-linking. Specific examples of heterocyclic di-N-oxides disclosed in the British patent include: pyrazine-1,4-di-N-oxide; quinoxaline-1,4-di-N-oxide; 2-acetyl-3-methyl quinoxaline-1,4-di-N-oxide; and 2,3-dimethyl quinoxaline-1,4-di-N-oxide. The cross-linked polymers described in the British patent are suggested as being useful as decorative or protective coatings and as ingredients for vehicle tires, hoses and other products.

U.S. Pat. No. 4,309,318 describes tread compositions for low rolling resistance tires comprising styrene-butadiene based rubber, carbon black and sulfur. Preferably the carbon black has an iodine adsorption number of 60–100 g$I_2$/kg and a DBP adsorption number of at least 119 cc/100 g.

European Published Patent Application No. 156,755 describes tires having sulfur-cured elastomeric tread compositions comprised of (a) medium vinyl polybutadiene, (b) 1,4-polyisoprene rubber, and (c) styrene/butadiene copolymer rubber. Tires constructed in this manner are reported to be characterized by improved rolling resistance without appreciable degradation of the wet and dry skid resistance and treadwear properties of the tires.

European Published Patent Application No. 159,469 relates to tire tread compounds comprising predominantly styrene-butadiene rubber reinforced with a special high structure (superfine) carbon black designated therein as N103. Tires made with such oil-extended tread formulations exhibit excellent abrasion resistance, traction and handling characteristics.

Rubber formulations useful for carcass and tread applications are described in U.S. Pat. No. 4,259,218. The formulations comprise a blend of medium vinyl polybutadiene and natural rubber reinforced with a carbon black having a highly negative tint residual.

SUMMARY OF THE INVENTION

It now has been found that uncured rubber compositions comprising rubbers having an unsaturated carbon chain and at least one carbon black can be improved by including therein, a minor property-improving amount of at least one aromatic heterocyclic di-N-oxide compound of the partial formula wherein the depicted carbon atoms are part of an optionally substituted aromatic ring, and $R^1$ and $R^2$ are each independently hydrogen, hydrocarbyl, halohydrocarbyl, hydrocarbyloxy, hydrocarbyl sulfonyl, hydrocarbyl thio, hydrocarbylsulfoxidyl, halogen, amino,

—CN

—OH

—CHO

—CH(O hydrocarbyl)$_2$

—C(O)R$^3$

—C(O)OR$^3$

—C(N—OH)R$^3$

—C(O)NR$^3$R$^6$

—CH=N—NH—C(O)OR$^3$

—CH$_2$OC(O)CH$_3$

—R$^4$YR$^3$

—C(O)NHR$^4$OH

—C(NH)NR$^7$R$^8$, or

—C(O)NHN(R$^3$)$_2$ wherein each $R^3$ is independently hydrogen or a hydrocarbyl group, $R^4$ is a divalent hydrocarbyl group, $R^6$ is hydrogen, hydrocarbyl, —R$^4$OR$^3$, or —R$^4$COOR$^3$; $R^7$ is hydrogen or a hydrocarbyl group; $R^8$ is hydrogen or a hydrocarbyl, an amino, or a hydroxyl group; $R^7$ and $R^8$ may be hydrocarbyl groups joined together to form a ring including the nitrogen atom, and Y is O, divalent S, —NH—, —S(O)— or —S(O)$_2$ or $R^1$ and $R^2$ may be joined together to form further ring systems which may be saturated or unsaturated, and further substituted or unsubstituted. When vulcanizates are prepared from such uncured rubber compositions, particularly when the carbon black used therein has an average surface area of at least about 20 m$^2$/g, the vulcanizates exhibit reduced low strain hysteresis and exhibit no significant undesirable odor.

In another aspect of the invention, a filled vulcanizate made by vulcanizing uncured compositions of the type described above and containing a filler, particularly carbon black, is improved in filler interaction, hysteresis, modulus, compression set and resiliency. Rubber articles and portions thereof made from such vulcanizates such as tires, hoses, belts, springs, treads, sidewalls and the like can be made utilizing the improved filled vulcanizates of the invention.

DETAILED DESCRIPTION OF THE INVENTION

The rubber compositions in one embodiment of this invention are not cured. In other words, they are not vulcanized. The uncured rubber compositions of the present invention are heterocyclic di-N-oxide modified rubber compositions which comprise (a) at least one rubber having an unsaturated carbon chain, (b) at least one carbon black, and (c) a minor, cured property-improving amount of at least one aromatic heterocyclic di-N-oxide compound of the partial formula

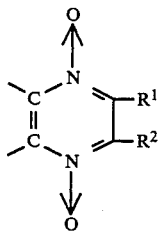

(I)

wherein the depicted carbon atoms are part of an optionally substituted aromatic ring, and $R^1$ and $R^2$ are each independently hydrogen, hydrocarbyl, halohydrocarbyl, hydrocarbyloxy, hydrocarbyl sulfonyl, hydrocarbyl thio, hydrocarbylsulfoxidyl, halogen, amino,

—CN

—OH

—CHO

—CH(O hydrocarbyl)$_2$

—C(O)R$^3$

—C(O)OR$^3$

—C(N—OH)R$^3$

—C(O)NR$^3$R$^6$

—CH=N—NH—C(O)OR$^3$

—CH$_2$OC(O)CH$_3$

—R$^4$YR$^3$

—C(O)NHR$^4$OH

—C(NH)NR$^7$R$^8$, or

—C(O)NHN(R$^3$)$_2$ wherein each $R^3$ is independently hydrogen or a hydrocarbyl group, $R^4$ is a divalent hydrocarbyl group, $R^6$ is hydrogen, hydrocarbyl, —R$^4$OR$^3$, or —R$^4$COOR$^3$; $R^7$ is hydrogen or a hydrocarbyl group; $R^8$ is hydrogen or a hydrocarbyl, an amino, or a hydroxyl group; $R^7$ and $R^8$ may be hydrocarbyl groups joined together to form a ring including the nitrogen atom, and Y is O, divalent S, —NH—, —S(O)— or —S(O)$_2$ or $R^1$ and $R^2$ may be joined together to form further ring systems which may be saturated or unsaturated, and further substituted or unsubstituted.

The rubbers in another aspect of this invention are vulcanizates (i.e., cured stocks) which are essentially the same as those described above. In addition to fillers of the conventional type such as carbon black and other inorganic, finely divided materials contained in uncured rubbers, the vulcanizates contain conventional curing systems and agents, such as sulfur, antioxidants, accelerators, retarders, coupling agents, promoters and the like.

The tires of the present invention have at least the outer circumferential tread portion thereof made from the uncured vulcanizable compositions described above. In one preferred embodiment the vulcanizable composition comprises a rubber (e.g., SBR), a carbon black filler having a surface area of at least about 20 m$^2$/g. and a minor property-improving amount of at least one aromatic heterocyclic di-N-oxide compound as defined herein. Other structural components of the tire such as the stabilizer ply insert, the sidewalls and/or belt can also be made from the same vulcanizable composition.

The rubbers used herein contain carbon-carbon unsaturation in the molecular structure and these rubbers include natural as well as synthetic rubbers. The rubber compositions used in the present invention include natural rubber and rubber-like polymers produced by polymerizing aliphatic, conjugated diolefins, especially those containing 4 to 8 carbon atoms per molecule such as butadiene, isoprene, pentadienes, etc., or the copolymers of such dienes. The rubbers used in the uncured compositions of this invention have unsaturated carbon chains. That is, their polymer backbones contain a significant amount of unsaturation, in contrast to the pendant or vinyl saturation found in some other types of rubbers. Typically, the chains of such unsaturated rubbers have at least about 5% of their carbon-to-carbon bonds as unsaturated bonds. Characterization of rubber as having unsaturated carbon chains is well known in the art as shown by ANSI/ASTM Standard D 1418-79A where unsaturated-chain rubbers are referred to as R rubbers. Class R rubbers include natural rubber and various synthetic rubbers derived at least partly from diolefins. The following is a non-exclusive list of R class rubbers which can be used in the compositions of the present invention:

ABR—Acrylate-butadiene
BR—Butadiene
CIIR—Chloro-isobutene-isoprene
CR—Chloroprene
IR—Isoprene, synthetic
NBR—Nitrile-butadiene
NCR—Nitrile-chloroprene
NIR—Nitrile-isoprene
NR—Natural rubber
SBR—Styrene-butadiene
SCR—Styrene-chloroprene
SIR—Styrene-isoprene rubbers.

Of these, the NR, IR, BR, SBR or mixtures of two or more of these are typically used. Many compositions are made wherein the rubber is NR, SBR or a mixture containing at least about 50% of one of these. Compositions containing only NR as the rubber portion are often used. In the context of this invention, NR includes both hevea and guayule rubber as well as mixtures thereof.

The rubbers used herein having carbon-carbon unsaturation also may be other than the R rubbers such as EPDM. EPDM rubbers are derived from ethylenepropylenediene monomer and generally about 3–8% of their carbon bonds are unsaturated bonds.

In one embodiment, the rubber compositions utilized in the preparation of at least the tread portion of the tires of the present invention is a styrene-butadiene rubber (SBR). Although the SBR is preferably 100% SBR, mixtures of SBR containing at least 50% SBR and less than 50% of other rubbers such as natural rubber (NR), butadiene rubber (BR), medium and high vinyl butadiene rubber, etc. may be used in some instances. In a preferred embodiment, however, the SBR used in the preparation of the vulcanizable compositions of this invention is 100% SBR and more typically 100% solution SBR.

The SBR used in the present invention includes SBR obtained by solution polymerization or emulsion polymerization. However, the solution SBR polymers are much preferred in this invention. The bound styrene content of the SBR used in the present invention may range from about 15 to about 40% by weight although it is preferred to use SBRs containing the higher amounts of bound styrene such as at least about 18% of bound styrene.

Carbon black fillers are included in the rubber compositions of this invention, and they include any of the commonly available, commercially-produced reinforcing carbon blacks. Those having a surface area (EMSA) of at least 20 m²/g. and more preferably at least 35 m²/g. up to 200 m²/g. or higher are preferred. Surface area values used in this application are those determined by ASTM test D-1765 using the cetyltrimethylammonium bromide (CTAB) technique. Among the useful carbon blacks are furnace black, channel blacks and lamp blacks. More specifically, examples of the carbon blacks include super abrasion furnace (SAF) blacks, high abrasion furnace (HAF) blacks, fast extrusion furnace (FEF) blacks, fine furnace (FF) blacks, intermediate super abrasion furnace (ISAF) blacks, semi-reinforcing furnace (SRF) blacks, medium processing channel blacks, hard processing channel blacks and conducting channel blacks. Other carbon blacks which may be utilized include acetylene blacks. Mixtures of two or more of the above blacks can be used in preparing the rubber compositions of the invention. Typical values for surface areas of usable carbon blacks are summarized in the following Table I.

TABLE I

| Carbon Blacks | |
|---|---|
| ASTM Designation (D-1765-82a) | Surface Area (m²/g) (D-3765) |
| N-110 | 126 |
| N-220 | 111 |
| N-339 | 95 |
| N-330 | 83 |
| N-550 | 42 |
| N-660 | 35 |

The carbon blacks utilized in the invention may be in pelletized form or an unpelletized flocculant mass. Preferably, for more uniform mixing, unpelletized carbon black is preferred. Similar silica reinforcing agents having comparable particle sizes and thus surface areas can also be used. The amount of carbon black included in the rubber compositions of the invention can vary over a wide range although amounts of from about 30-80 parts of carbon black per 100 parts of rubber (phr) are generally used.

The above rubber compositions can be modified in accordance with the present invention by incorporating into the rubber a minor property-improving amount of at least one aromatic heterocyclic di-N-oxide compound as defined and illustrated more fully below. The amount of the heterocyclic di-N-oxide incorporated into the unvulcanized rubber composition will generally be an amount which is sufficient to provide desirable properties to the rubber composition in its uncured as well as cured form. Thus, the amount of the heterocyclic di-N-oxide incorporated into an uncured formulation will be an amount which will improve the processability of the composition, and in certain instances, its green strength and/or viscosity properties. Processability properties are those related to the ease and efficiency of mixing, mastication and handling of a rubber composition in its unvulcanized, that is, uncured state. Similar amounts are used in the cured compositions to improve such vulcanizate properties as filler interaction, modulus, resiliency, hysteresis, rolling loss, running temperature and the like. Typically, this property-improving amount will range from about 0.1 to about 10 parts per 100 parts by weight of rubber (phr). More often, the heterocyclic di-N-oxide will be used in an amount ranging from about 0.5 to 3 phr.

In one embodiment, the heterocyclic di-N-oxides used in both the vulcanizable and vulcanized (cured) rubber compositions of this invention are aromatic heterocyclic di-N-oxide compounds of the partial formula

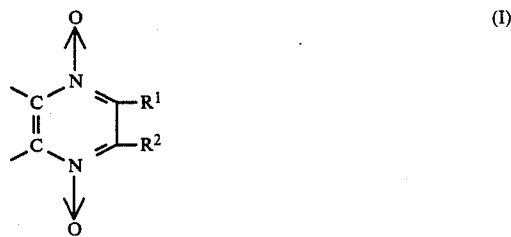

(I)

wherein the depicted carbon atoms are part of an optionally substituted aromatic ring, and $R^1$ and $R^2$ are each independently hydrogen, hydrocarbyl, halohydrocarbyl, hydrocarbyloxy, hydrocarbyl sulfonyl, hydrocarbyl thio, hydrocarbylsulfoxidyl, halogen, amino,

—CN

—OH

—CHO

—CH(O hydrocarbyl)$_2$

—C(O)R$^3$

—C(O)OR$^3$

—C(N—OH)R$^3$

—C(O)NR$^3$R$^6$

—CH=N—NH—C(O)OR$^3$

—CH$_2$OC(O)CH$_3$

—R$^4$YR$^3$

—C(O)NHR⁴OH

—C(NH)NR⁷R⁸, or

—C(O)NHN(R³)₂ wherein each $R^3$ is independently hydrogen or a hydrocarbyl group, $R^4$ is a divalent hydrocarbyl group, $R^6$ is hydrogen, hydrocarbyl, —R⁴OR³, or —R⁴COOR³; $R^7$ is hydrogen or a hydrocarbyl group; $R^8$ is hydrogen or a hydrocarbyl, an amino, or a hydroxyl group; $R^7$ and $R^8$ may be hydrocarbyl groups joined together to form a ring including the nitrogen atom, and Y is O, divalent S, —NH—, —S(O)— or —S(O)₂ or $R^1$ and $R^2$ may be joined together to form further ring systems which may be saturated or unsaturated, and further substituted or unsubstituted. The aromatic ring which includes the depicted carbon atoms may be carbocylic such as a benzene ring, or it may be heterocyclic such as a pyridine ring. It may be the only additional ring in the di-N-oxide compound, or it can be part of a linked or fused ring system. It is necessary only that the depicted carbon atoms be part of the same aromatic ring.

In the above Formula I, any one or two of any ring positions which may be present can be substituted with halogen and/or hydroxyl, cyano hydrocarbyl, hydrocarbyloxy, hydrocarbylthio, hydrocarbylcarbonyl, nitro, amino —C(O)-hydrocarbyl or ester groups. The hydrocarbyl groups may be alkyl, aryl, alkaryl, aralkyl, etc., and the hydrocarbyloxy groups may be the corresponding alkoxy, aryloxy, etc. groups.

The group $R^3$ may be a lower hydrocarbyl group as defined above or a higher hydrocarbyl group such as an aliphatic group containing from 8 to 30 carbon atoms including decyl, dodecyl, tridecyl, hexadecyl, etc. The group $R^4$ is a divalent hydrocarbyl group and is generally a divalent lower hydrocarbyl group such as methylene, ethylene, propylene, etc.

Examples of various aromatic heterocyclic di-N-oxide compounds which are illustrative of Formula I can be represented by the following formulae

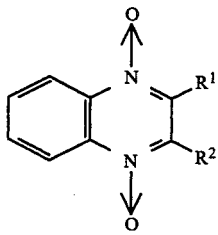
(Ia)

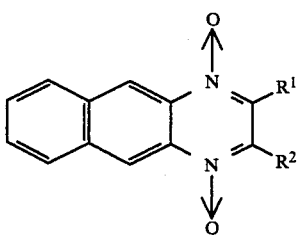
(Ib)

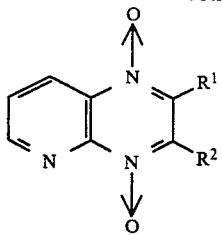
(Ic)

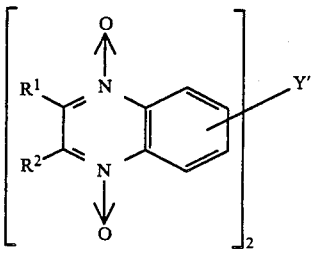
(Id)

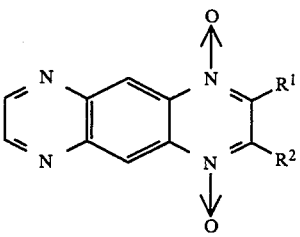
(Ie)

wherein $R^1$ and $R^2$ are as defined with respect to Formula I and wherein, none, one, or any two of the other ring positions can be substituted with hydrocarbyl, hydrocarbyloxy, hydrocarbylthio, hydroxyl, halogen, cyano, nitro, amino, amide, ester or —C(O)-hydrocarbyl groups, and Y' is a linking atom or group. Linking atoms of groups (Y') include ether, thioether, sulfoxide, sulfone, amine, methylene, etc. (including simple covalent bonds such as found in biphenyl).

As mentioned above, $R^1$ and $R^2$ in Formula I may be hydrocarbyl groups joined together to form further ring systems which may be saturated or unsaturated and further substituted or unsubstituted. Such compounds may be represented by the following Formula II

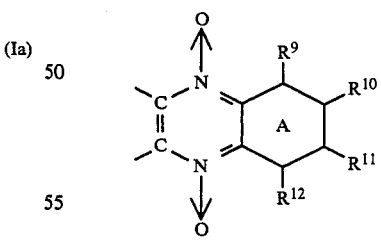
(II)

wherein the depicted carbon atoms are part of an aromatic ring which may be substituted, ring A is aromatic or non-aromatic, $R^9$, $R^{10}$, $R^{11}$ and $R^{12}$ are each independently hydrogen or a hydrocarbyl, hydrocarbyloxy, hydrocarbylthio, hydroxyl amino, nitro carboxylic, carboxylic ester, amide, or cyano group, and when ring A is an aromatic ring, any two or more adjacent groups may be joined together to form additional aromatic rings. The hydrocarbyl, hydrocarbyloxy and hydrocarbylthio groups may contain up to about 30 carbon atoms although the hydrocarbyl groups generally will be lower hydrocarbyl groups as defined above. When any of the $R^9$ through $R^{12}$ groups are hydrocarbyloxy or hydrocarbylthio, the hydrocarbyl groups may be either lower hydrocarbyl or higher hydrocarbyl groups also as defined above. In one preferred embodiment, $R^6$ through $R^9$ are hydrogen and ring A is a saturated ring.

In a preferred embodiment, the aromatic heterocyclic di-N-oxides useful in the present invention are represented by Formula III

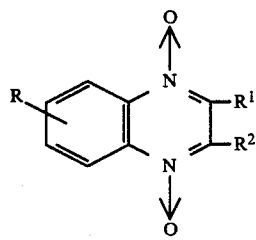

(III)

wherein $R^1$ and $R^2$ are defined in Formula I and R is hydrogen or a hydrocarbyl, hydrocarbyloxy, hydrocarbylthio, hydroxyl, halogen, cyano, amino, amide, ester or —C(O)-hydrocarbyl group.

As mentioned, $R^1$ and $R^2$ in Formula III may by hydrocarbyl groups joined together to form further ring systems which may be illustrated by the following formulae

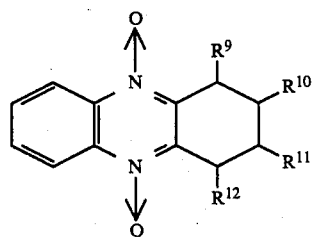

(IIa)

wherein $R^9$, $R^{10}$, $R^{11}$, and $R^{12}$ are as defined with respect to Formula II above and wherein none, one or any two of the aromatic ring positions may be substituted with a hydrocarbyl, hydrocarbyloxy, hydrocarbylthio, hydroxyl, halogen, cyano, nitro, amino or —C(O)-hydrocarbyl groups;

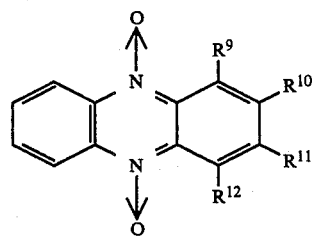

(IIb)

wherein $R^1$, $R^9$, $R^{10}$, $R^{11}$, and $R^{12}$ are as defined above with respect to Formula IIa, and wherein none, one or any two of the other aromatic positions can be substituted with hydrocarbyl, halogen, hydroxyl, hydrocarbyloxy, hydrocarbylthio, hydrocarbylcarbonyl, amino, amide, ester, or —C(O)-hydrocarbyl groups, and any two or more adjacent R groups may be joined together to form additional aromatic rings; and

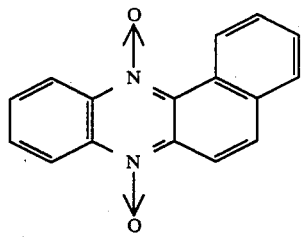

(IIb-1)

wherein none, one, or any of the ring positions can be substituted with hydrocarbyl, hydrocarbyloxy, hydrocarbylthio, halogen, hydroxyl, hydrocarbyl carbonyl, nitro, sulfonyl, carboxyl, or amino groups.

In another embodiment of the invention, the heterocyclic di-N-oxide is further characterized by the formula

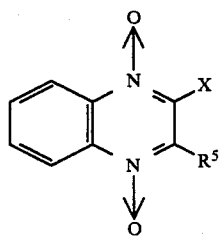

(IV)

wherein X is —OH, —CN, —C(O)OR$^3$, —C(-N—OH)R$^3$, —CHO, —CH(O—hydrocarbyl)$_2$, —C(O)NHR$^6$, —C(O)NHN(R$^3$)$_2$, —R$^4$YR$^3$, —C(NH)NR$^7$R$^8$, or —C(O)NHR$^4$OH; R$^5$ is X, hydrogen, a hydrocarbyl, a halohydrocarbyl or hydrocarbyloxy group; R$^3$ is hydrogen or a hydrocarbyl group; R$^4$ is a divalent hydrocarbyl group; R$^6$ is hydrogen, —R$^4$COOR$^3$ or —R$^4$YR$^3$; R$^7$ is hydrogen or a hydrocarbyl group; R$^8$ is hydrogen or a hydrocarbyl, an amino, or a hydroxyl group; or R$^7$ and R$^8$ may be hydrocarbyl groups joined together to form a ring system including the nitrogen atom, and Y is O or divalent S; or X and R$^5$ are hydrocarbyl groups joined together to form further ring systems which are saturated or unsaturated, and further substituted or unsubstituted. Further examples of di-N-oxides of the type represented by Formula IV include the compounds contained within Formulae II and III by substituting X and R$^5$ for R$^1$ and R$^2$, respectively.

The aromatic heterocyclic di-N-oxides useful in the compositions of the present invention can be prepared by methods known in the art. For example, heterocyclic di-N-oxides can be prepared from various benzofurazan-N-oxides by reacting the furazan N-oxides with, for example, aldehydes, ketones, enamines, enolate anions, etc. This reaction has become known as the Beirut reaction and extensive reviews of such reactions have been published. See, for example, M. J. Haddadin et al, Tetrahedron, 32, 719 (1976); K. Ley and F. Seng, Syntheses, 415–422 (1975); M. J. Haddadin et al, Heterocycles 4, 767 (1976); M. J. Haddadin, and G. H. Issidorides, J. Org. Chem. 37, 589 (1972); J. W. McFarland, J. Org. Chem. 36, 1842 (1971); E. Abushanab J. Org. Chem. 35 4279 (1970); and A. Gasco and A. J. Boulton, Advances in Heterocyclic Chem., Vol. 29, 306 Academic Press, 1981. The disclosures of these publications relating to the preparation of various heterocyclic di-N-oxides of the types represented by Formulae II, III and IV, IIa, IIb, IIb-1, are hereby incorporated by reference.

Specific examples of aromatic heterocyclic di-N-oxides which have been described in the above literature and which can be used in preparing the rubber compositions of the present invention include those identified in the following Table II.

TABLE II

HETEROCYCLIC DI—N—OXIDES
Examples H-1 to H-46

|      | R¹              | R²                         | R       |
|------|-----------------|----------------------------|---------|
| H-1  | CN              | CH₃                        | H       |
| H-2  | —C(O)NHC₂H₄OH   | CH₃                        | H       |
| H-3  | —C(O)NHC₃H₇     | CH₃                        | OCH₃    |
| H-4  | C(N—OH)—CH₃     | CH₃                        | H       |
| H-5  | CH₂SC₁₂H₂₅      | CH₃                        | H       |
| H-6  | OH              | CH₃                        | H       |
| H-7  | CH₂OC₁₂H₂₅      | CH₃                        | H       |
| H-8  | CH₃             | CH₃                        | H       |
| H-9  | CH(CH₃)₂        | CH₃                        | H       |
| H-10 | C(O)CH₃         | CH₃                        | H       |
| H-11 | H               | H                          | H       |
| H-12 | SCH₃            | CH₃                        | H       |
| H-13 | S(O)CH₃         | CH₃                        | H       |
| H-14 | S—C₆H₅          | CH₃                        | H       |
| H-15 | CN              | NH₂                        | CH₃     |
| H-16 | CN              | OH                         | CH₃     |
| H-17 | H               | CH₃                        | H       |
| H-18 | C₂H₅            | CH₃                        | OCH₃    |
| H-19 | CH₃             | CH(CH₃)₂                   | C(O)NH₂ |
| H-20 | CH₃             | C₈H₁₂                      | H       |
| H-21 | C₁₅H₃₃          | CH₃                        | H       |
| H-22 | C(O)NH₂         | NH₂                        | H       |
| H-23 | C(O)NH₂         | C(O)NH₂                    | H       |
| H-24 | C(O)NH₂         | OH                         | CH₃     |
| H-25 | C(NH)NHOH       | OH                         | H       |
| H-26 | C(NH)NHNH₂      | NH₂                        | H       |
| H-27 | C(NH)—N         | CH₃                        | CH₃     |
| H-28 | C(NH)N(CH₃)₂    | OH                         | H       |
| H-29 | OH              | OH                         | OC₂H₅   |
| H-30 | CH₃             | C(O)NHC₂H₄OCH₃             | H       |
| H-31 | CH₃             | C(O)NHCH₂COOH              | H       |
| H-32 | CH₃             | C(O)CH₃                    | H       |
| H-33 | CH₂Cl           | C(O)NHN(CH₃)₂              | H       |
| H-34 | CH₃             | COOEt                      | H       |
| H-35 | H               | CHO                        | H       |
| H-36 | H               | CH(OMe)₂                   | H       |
| H-37 | CH(OMe)₂        | CHO                        | H       |
| H-38 | CH₂Cl           | C(O)NHCH₃                  | H       |
| H-39 | p-NO₂C₆H₄—      | H                          | H       |
| H-40 | p-BrC₆H₄        | H                          | H       |
| H-41 | COCH₃           | C₆H₅                       | H       |
| H-44 | CH₃             | CH₃                        | CONH₂   |
| H-45 | CH₃             | CH₃                        | C(O)OCH₃|
| H-46 | CH₃             | CH₃                        | Cl      |

Example H-47A    47B

Example H-48

Example H-49

Examples H-50 to H-64

|      | R⁹    | R¹⁰     | R¹¹       | R¹²    |
|------|-------|---------|-----------|--------|
| H-50 | H     | OH      | H         | Cl     |
| H-51 | H     | OH      | H         | H      |
| H-52 | H     | OH      | CH₃       | H      |
| H-53 | H     | OH      | C(CH₃)₃   | H      |
| H-54 | H     | OH      | H         | COCH₃  |
| H-55 | H     | OH      | CH₃       | CH₃    |
| H-56 | COCH₃ | OH      | H         | H      |
| H-57 | NO₂   | OH      | H         | H      |
| H-58 | H     | NH₂     | H         | H      |
| H-59 | H     | OH      | OH        | H      |
| H-60 | H     | —OCH₂O— |           | H      |
| H-61 | H     | OH      | OCH₃      | H      |
| H-62 | H     | OH      | H         | OH     |
| H-63 | H     | OH      | OH        | CH₃    |
| H-64 | H     | OH      | CO₂CH₃    | H      |

Examples H-65 to H-73

TABLE II-continued

[Structure: phenazine di-N-oxide with R13, R14 on one ring and R15, R16 positions]

| | R13 | R14 | R15 | R16 |
|---|---|---|---|---|
| H-65 | H | H | H | H |
| H-66 | H | H | H | COOH |
| H-67 | H | H | H | $NH_2$ |
| H-68 | $NHSO_2CH_3$ | H | H | H |
| H-69 | $NHCOCH_3$ | H | H | H |
| H-70 | H | $NO_2$ | $SO_3Na$ | H |
| H-71 | $NH_2$ | $SO_3H$ | H | H |
| H-72 | H | $SO_3Na$ | H | $SO_3Na$ |
| H-73 | $SO_3Na$ | H | H | COOH |

Example H-74

[Structure of example H-74 compound]

Example H-75

[Structure of example H-75 compound]

The vulcanizable compositions of the present invention comprising at least one rubber, at least one carbon black, and at least one aromatic heterocyclic di-N-oxide compound can be prepared by conventional techniques using various types of mills, blenders and mixers known to the art. It is important to the present invention that the rubber, carbon black, heterocyclic di-N-oxide, and any other normal compounding additives be mixed at an elevated temperature. Thus, mixing of the ingredients is effected at temperatures in excess of about 140° C. and more generally above about 150° C. Most often, the temperature of the rubber mixes as it is removed from an internal mixer at about 170°–190° C. Examination of this rubber mix often reveals a reduction in the molecular weight of the rubber. When vulcanized, the vulcanizates prepared from such rubber mixes exhibit a reduction in hysteresis.

Specifically, devices such as well-known Brabender and Banbury mixers can be used to mechanically compound the rubber, carbon black and the heterocyclic di-N-oxide compound together with any fillers such as carbon black, and other materials generally used in conventional rubber formulations such as antioxidants, retarders, etc. as mentioned above. To achieve the improved properties, the vulcanizable mixtures of the present invention are compounded at the above indicated temperatures for a period of from about 2 to about 20 minutes, generally from about 3 to about 15 minutes. For example, when a conventional size Banbury mixer (1300 cc) is used, the apparatus is operated at a rotor speed of about 50 to about 150 rpm. while a laboratory 65 cc. Brabender apparatus is operated at a mixing speed of about 60–100 rpm. Such devices can be equipped with thermocouples and water jackets to monitor and control mixing batch temperature. Generally, the cavity is preheated before adding the materials to be mixed. Finishing steps can be carried out on conventional equipment such as open mills using conditions and techniques known to the art. Similarly, tread components for pneumatic tires can be prepared by conventional procedures.

In some instances, it is convenient to combine the heterocyclic di-N-oxide with an inert material which serves as a carrier and de-sensitizer. Organic materials such as methyl stearate, petroleum wax, viscous mineral oils as well as inorganic and mixed materials such as clay, zinc stearate, diatomaceous earth and the like can be used for this purpose. Such combinations usually contain about 25–95% of the heterocyclic di-N-oxide with the balance being one or more of the inert materials.

In addition to the heterocyclic di-N-oxides, the uncured rubber compositions of this invention also may contain materials used in conventional rubber formulations such as antioxidants, retarders, promoters, fillers, etc. In the uncured or unvulcanized rubber compositions of the invention, the compositions do not contain curing agents, either because they are intermediate compositions to which a curing system will be, but not yet has been, added or because they are to be put in use without the addition of curing agents in such applications as sealants, caulks, adhesives, etc.

As mentioned above, fillers in addition to the carbon black may be present in the uncured rubber compositions of the present invention. Typical fillers include glass, silica, caulk, and similarly finely divided mineral materials. The amount of filler incorporated into the rubber compositions of the present invention may be varied over a wide range although the mixture generally will contain from about 30 to 100 parts of filler per 100 parts of rubber.

The following examples illustrate the preparation of the di-N-oxide modified uncured rubber compositions of the present invention. Unless otherwise indicated in the examples or elsewhere in the application, all parts and percentages are by weight, and the temperatures are in degrees centigrade. In the following examples, solution SBR-1 is an SBR in 37.5 phr aromatic oil further characterized as containing 25% bound styrene and 2.5% max. block styrene, with a Mooney Viscosity: Large Rotor/4 at 212° F. of 45±5. Solution SBR-2 contains 20 phr Sundex 750T oil and the SBR contains 35% bound styrene and 3.8% max. block styrene. The Mooney Vicsosity: Small Rotor/4 at 212° F. is 41±5.0. Solution SBR-3 contains 37.5 phr of aromatic oil and the SBR contains 18% bound styrene and 1.5% max. block styrene. The Mooney: Large Rotor/4 at 212° F. is 45±5.

Unless otherwise indicated, an internal mixer, such as a Brabender or small size (65 cc cavity) Banbury mixer is used to prepare the uncured rubber formulations. The usual technique is to add various parts of the composition to the preheated cavity of the mixer, continuing the mixing for the indicated period of time, and then making further additions. The standard technique is according to the following procedure.

| Time | Add to Mixer |
|------|--------------|
| 0 | Rubber, 100 parts |
| 0.5 | Half charge carbon black plus heterocyclic di-N—oxide |
| 1.5 | Balance of carbon black plus zinc oxide, stearic acid, etc. |
| 3.0 | Processing oil if desired |
| 6.0 | Drop mixed compositions at about 170–190° C. (340–380° F.) |

Masterbatches prepared essentially according to this schedule can be combined with the conventional elastomer curing systems described in the following examples in typical amounts and cured for 15–30 minutes at about 150° C. to provide test specimens.

TABLE III

| UNCURED RUBBER FORMULATIONS | | | | | | | | | |
|---|---|---|---|---|---|---|---|---|---|
| Example/pbw | 1 | 2 | 3 | 4 | 5 | 6 | 7 | 8 | 9 |
| Solution SBR-1 | 137.5 | → | → | → | → | → | → | → | → |
| Carbon black (N339) | 63 | → | → | → | → | → | → | → | → |
| ZnO | 1.6 | → | → | → | → | → | → | → | → |
| Stearic acid | 4.0 | → | → | → | → | → | → | → | → |
| Product | | | | | | | | | |
| H-1 | 1.0 | | | | | | | | |
| H-3 | | 1.0 | | | | | | | |
| H-4 | | | 1.0 | | | | | | |
| H-5 | | | | | | | | 1.0 | |
| H-8 | | | | | | | | | 1.0 |
| H-51 | | | | 1.0 | 0.5 | 1.5 | 2.0 | | |

TABLE IV

| UNCURED RUBBER FORMULATIONS | | |
|---|---|---|
| Example/pbw | 10 | 11 |
| Solution SBR-1 | 137.5 | 137.5 |
| Carbon black (N339) | 63 | 63 |
| Stearic acid | 1.5 | 1.5 |
| Product H-2 | 1.5 | 2.5 |

TABLE V

| UNCURED RUBBER FORMULATIONS | | | |
|---|---|---|---|
| Example/pbw | 12 | 13 | 14 |
| Solution | | | |
| SBR-2 | 60.5 | 60.5 | 120 |
| SBR-3 | 68.75 | 68.75 | — |
| Carbon black (N339) | 63 | 63 | 60 |
| ZnO | 3 | 3 | 5 |
| Stearic acid | 2 | 2 | 2 |
| Wax | 2 | 2 | — |
| Santoflex 13 | 1 | 1 | 1.5 |
| Aromatic oil | 2 | 2 | — |

TABLE V-continued

| UNCURED RUBBER FORMULATIONS | | | |
|---|---|---|---|
| Example/pbw | 12 | 13 | 14 |
| Product | | | |
| H-47A | 1.5 | — | — |
| H-65 | — | 1.0 | 1.5 |

As mentioned above, the uncured carbon-containing di-N-oxide modified rubber compositions of the invention are useful in the preparation of vulcanizates which are useful in a number of applications. Thus, the uncured modified rubber compositions of the present invention generally are formulated with conventional rubber additives to form masterbatches which can then be cured by the addition of curing agents, accelerators, etc.

The curing agents used to prepare the vulcanizates may be conventional types such as sulfur- or peroxide-based curing systems. They are used in conventional amounts and incorporated in the uncured compositions of the invention by known techniques and procedures. The vulcanizates of this invention are prepared by curing these compositions under conditions of temperature and time customarily used in the art. Typically, the rubber, heterocyclic di-N-oxide, carbon black, other fillers and normal processing aids such as zinc oxide, stearic acid and processing oil are mixed, the sulfur and accelerators are then added, and the mixture is cured. Other mixing sequences can be used, but it is preferred to have the rubber, di-N-oxide, and carbon black composition intimately combined before vulcanization.

Among the desirable and beneficial properties exhibited by the vulcanized rubber compositions of the present invention prepared with the uncured di-N-oxide modified rubber compositions described herein are an increase in rebound, and reduced low strain hysteresis, and when utilized in treads of tires, a decrease in the rolling loss and/or running temperature.

The following examples illustrate the preparation of vulcanized rubber compositions in accordance with the invention utilizing the di-N-oxide modified rubbers of the invention. Conventional rubber compounding materials, conditions, temperatures, procedures and evaluation techniques are used unless noted to the contrary. Generally test speciments are obtained by curing the stock for 15–30 minutes at about 150° C.

EXAMPLES A–F

Passenger tire tread vulcanizates are prepared from a solution SBR-1 according to a tread stock recipe containing: 137.5 parts of SBR-1, 63 phr of carbon black (N339), 1.6 phr of ZnO, 4.0 phr of stearic acid, 3.83 phr of sulfur, 1 phr of Santocure NS, and 1.0 phr of the heterocyclic di-N-oxides in accordance with the invention. A control stock is also prepared containing no di-N-oxide. The formulations are mixed and cured in the usual manner, and the vulcanizate specimens evaluated in a number of standard tests. The results of the tests are summarized in Table VI.

TABLE VI

| Example/ di-N—oxide | Control (None) | A (H-1) | B (H-3) | C (H-4) | D (H-5) | E (H-8) | F (H-65) |
|---|---|---|---|---|---|---|---|
| Monsanto Rheom. 300° F. | | | | | | | |
| TS(2) | 9.48 | 13.06 | 10.3 | 12.1 | 10.3 | 12.58 | 11.16 |
| TC(90) | 23.2 | 26.06 | 25.2 | 25.9 | 25.9 | 25.84 | 24.12 |
| Min. Torque | 12.2 | 10.5 | 8.1 | 7.7 | 7.5 | 13.4 | 11.5 |

TABLE VI-continued

| Example/di-N—oxide | Control (None) | A (H-1) | B (H-3) | C (H-4) | D (H-5) | E (H-8) | F (H-65) |
|---|---|---|---|---|---|---|---|
| Max. Torque | 43.0 | 41.2 | 40.2 | 40.2 | 37.9 | 43.2 | 41.5 |
| % Rebound | | | | | | | |
| 73° F. | 40 | 45.5 | 45 | 44 | 44 | 44.0 | 46.5 |
| 212° F. | 69 | 72.5 | 70 | 72 | 70 | 70.0 | 71.5 |
| MTS 7% def. 10 lb. 10 HZ | | | | | | | |
| K'(73° F.) | 1270 | 1120 | 1200 | 1190 | 1140 | 1240 | 1140 |
| K"(73° F.) | 298 | 218 | 253 | 242 | 238 | 268 | 228 |
| Tan delta | 0.235 | 0.195 | 0.211 | 0.204 | 0.209 | 0.216 | 0.200 |
| % delta change | Par | −17 | −10 | −13 | −11 | −8 | −15 |
| Shore "A" Hardness | | | | | | | |
| 73° F. | 66 | 64 | 70 | 63 | 67 | 67 | 64 |
| 212° F. | — | — | 65 | 66 | 64 | — | — |
| Resistivity (K ohms) | 97 | 490 | — | — | — | 200 | 200 |

EXAMPLES G AND I-K

Tire tread vulcanizates are prepared from a solution SBR-1 tread stock recipe similar to Example F except that the level of the di-N-oxide (H-50) is 0.5, 1.0, 1.5 and 2.0 phr. Batches are mixed in a Brabender which has been preheated to 170° C. The drop temperature is 370° F. (188° C.) after a 6-minute mix. Final mixtures are prepared on a small mill. The batches appear to become softer as the level of di-N-oxide is increased, and the batches are very smooth with no evidence of cross-linking or odor. The vulcanizate specimens prepared in this manner are evaluated in a number of standard tests, and the results of the tests are summarized in Table VII. As can be seen, the use of the di-N-oxide Examples G and I-K results in up to a 31% reduction in tan delta and an increase in percent rebound of 9% at 73° F. A large increase in electrical resistivity also is observed. The data summarized in Table VII demonstrate that the di-N-oxide of Example H-50 functions as a very effective promoter in SBR without odor or cross-linking problems.

EXAMPLES G AND I-K:

TABLE VII

| Example/Level (phr) | Control (None) | G (0.5) | I (1.0) | J (1.5) | K (2.0) |
|---|---|---|---|---|---|
| Monsanto Rheom. 300° F. | | | | | |
| TS(2) | 5.54 | 6.48 | 6.42 | 6.19 | 6.0 |
| TC(90) | 12.67 | 13.6 | 13.55 | 13.3 | 13.7 |
| Min. Torque | 7.6 | 6.9 | 6.2 | 6.2 | 5.1 |
| Max. Torque | 37.6 | 37.5 | 36.7 | 37.0 | 36.3 |
| % Rebound | | | | | |
| 73° F. | 42 | 45 | 47.5 | 47.5 | 51 |
| 212° F. | 70 | 72.5 | 74 | 75 | 78 |
| MTS 7% def. 10 lb. 10 HZ | | | | | |
| K'(73° F.) | 1110 | 1040 | 990 | 1000 | 920 |
| K"(73° F.) | 245 | 206 | 175 | 172 | 141 |
| Tan delta | 0.221 | 0.198 | 0.177 | 0.172 | 0.152 |
| % delta change | Par | −10.4 | −20 | −22 | −31 |
| Shore "A" Hardness | | | | | |
| 73° F. | 67 | 67 | 66 | 66 | 66 |
| 212° F. | 62 | 63 | 63 | 63 | 63 |
| Resistivity (K ohms) | 0.32 | 1.23 | 5.0 | 16.4 | 40 |

EXAMPLES L-M

Tire tread vulcanizates are prepared from a solution SBR-1 tread stock recipe containing 137.5 parts of SBR-1 solution, 63 phr of N-339 carbon black, 1.5 phr of stearic acid, 5 phr of ZnO, 1.0 phr of Santocure NS, 1.8 phr of sulfur and either 1.5 or 2.5 phr of the di-N-oxide H-2. A control vulcanizate is also prepared containing no H-2. The results of the evaluation of the vulcanizates are summarized in Table VIII.

TABLE VIII

| Example/Level (phr) | Control (None) | L (0.5) | M (1.0) |
|---|---|---|---|
| Monsanto Rheom. 300° F. | | | |
| TS(2) | 16.3 | 17.05 | 16.6 |
| TC(90) | 26.4 | 27 | 26.7 |
| Min. Torque | 9.7 | 9.4 | 9.9 |
| Max. Torque | 30.7 | 31 | 32 |
| % Rebound | | | |
| 73° F. | 42 | 45 | 45 |
| 212° F. | 55 | 59 | 59 |
| MTS 7% def. 10 lb. 10 HZ | | | |
| K'(73° F.) | 890 | 890 | 940 |
| K"(73° F.) | 203 | 181 | 189 |
| Tan delta | 0.229 | 0.201 | 0.202 |
| % delta change | Par | −11 | −12 |
| Shore "A" Hardness | | | |
| 73° F. | 62 | 62 | 63 |
| 212° F. | 57 | 56 | 58 |

EXAMPLES N-O

A series of vulcanizates is prepared from a typical SBR tire tread formulation containing a mixture of SBR-2, SBR-3, conventional processing aids, and 1 phr of the product H-65 (Example N) or 1.5 phr of the product H-47A (Example O). A control stock also is prepared containing no di-N-oxide. The formulations are mixed and cured in the usual manner, and the vulcanizate specimens are evaluated in a number of standard tests. The results of the tests are summarized in Table IX.

TABLE IX

| Example/Level (phr) | Control (None) | N (H-65 @ 1.0) | O (H-47A @ 1.5) |
|---|---|---|---|
| Monsanto Rheom. 300° F. | | | |
| TS(2) | 14.5 | 14.4 | 11.9 |
| TC(90) | 27.0 | 27.1 | 22.3 |
| Min. Torque | 9.5 | 7.9 | 8.4 |
| Max. Torque | 32.6 | 32.9 | 31.2 |
| MTS 7% def. 10 lb. 10 HZ | | | |
| K'(73° F.) | 1030 | 920 | 910 |
| K"(73° F.) | 217 | 153 | 165 |
| Tan delta | 0.211 | 0.167 | 0.182 |
| % delta change | Par | −21 | −14 |
| K'(150° F.) | 790 | 740 | 740 |
| K"(150° F.) | 132 | 86 | 95 |
| Tan delta | 0.168 | 0.116 | 0.128 |
| % delta change | Par | −31 | −24 |
| Shore "A" Hardness | | | |
| 73° F. | 63 | 62 | 61 |
| 212° F. | 60 | 59 | 57 |

EXAMPLES P, Q AND R

In these examples, the heterocyclic di-N-oxide product H-65 is evaluated in a solution SBR-2 formulation at a level of 1.5 phr. A control master batch also is prepared which does not contain product H-65. Each of the two masterbatches is divided into three finals in which high, intermediate and low cross-link density samples are prepared using varying amounts of Santocure NS and sulfur. The masterbatches are mixed in a Banbury and dropped at 380° F. The formulations are shown in Table X, and the properties of the vulcanizates are summarized in Table XI. As can be seen from the results in Table XI, product H-65 reduces the Mooney viscosity and has substantially no effect on the cure characteristics. Product H-65 shows little effect on compression set or durometer, but reduces tan delta by 20 to 28%. The results also show that electrical resistivity is increased by product H-65, and Pico abrasion is not significantly changed.

TABLE X
EVALUATION OF BENZOPHENAZINE DIOXIDE: FORMULATIONS

| Example | Cont-1 | Cont-2 | Cont-3 | P | Q | R |
|---|---|---|---|---|---|---|
| SOL. SBR-2 | 120 | → | → | 120 | → | → |
| HAF N339 | 60 | → | → | 60 | → | → |
| ZnO | 5 | → | → | 5 | → | → |
| Stearic acid | 2 | → | → | 2 | → | → |
| Santoflex 13 | 1.5 | → | → | 1.5 | → | → |
| Product H-65 | — | — | → | 1.5 | → | → |
| Santocure NS | 2.5 | 1.0 | .5 | 2.5 | 1.0 | .5 |
| Sulfur | 3.3 | 1.8 | 1.3 | 3.3 | 1.8 | 1.3 |

TABLE XI
EVALUATION OF BENZOPHENAZINE DIOXIDE: PROPERTIES

| Example | Cont-1 | Cont-2 | Cont-3 | P | Q | R |
|---|---|---|---|---|---|---|
| Monsanto Rheom. 300° F. | | | | | | |
| TS2 | 8.7 | 11.6 | 15.2 | 9.5 | 12.1 | 16.7 |
| TC90 | 14.8 | 22.7 | 35.1 | 14.8 | 23.6 | 35.9 |
| Shore "A" Hardness | | | | | | |
| 73° F. | 73 | 65 | 63 | 72 | 66 | 63 |
| 212° F. | 72 | 63 | 56 | 70 | 61 | 54 |
| Comp. Set 22 Hrs. @ 158° F. | | | | | | |
| 16.8 | 20 | 39.2 | 16.8 | 20.3 | 40.6 | |
| MTS 7% Defl. 10# 10 HZ | | | | | | |
| K' 73° F., K" | 1420 | 1130 | 1040 | 1240 | 1040 | 960 |
| | 248 | 241 | 239 | 156 | 177 | 178 |
| Tan delta | .175 | .214 | .229 | .126 | .170 | .185 |
| % delta change | Par | — | — | −28 | −21 | −19 |
| 150° F. | | | | | | |
| Tan delta | .149 | .175 | .210 | .101 | .143 | .172 |
| % delta change | Par | — | — | −32 | −18 | −18 |
| % Rebound | | | | | | |
| 73° F. | 39 | 38 | 38 | 42 | 42 | 42 |
| 150° F. | 65 | 59.5 | 55.5 | 73.5 | 64 | 60 |
| Ring Tear (ppi) | | | | | | |
| 212° F. | 74 | 269 | 374 | 52 | 144 | 271 |
| % delta change | Par | — | — | −29 | −46 | −27 |
| 340° F. | 33 | 196 | 240 | 32 | 85 | 155 |
| Electrical Resistivity $10^6$ ohm | .3 | .8 | .4 | 120 | 10 | 20 |
| Pico Index | 2.8336 | 1.8615 | 1.2653 | 2.9179 | 1.7212 | 1.3331 |

EXAMPLES S AND T

Tire tread stock formulations are prepared from 137.5 parts of solution SBR-1, 63 phr of carbon black N-339, 5 phr of ZnO, 1.5 phr of stearic acid, 1.0 phr of Santocure NS, 1.8 part of sulfur, and 1.0 phr of heterocyclic di-N-oxide H-9 or H-47A. A control stock is prepared containing no di-N-oxide. The formulations are mixed and cured in the usual manner, and vulcanizate specimens are evaluated. The results of the evaluations are summarized in Table XII.

TABLE XII

| Example/Level (phr) | Control (None) | S (H-47A) | T (H-9) |
|---|---|---|---|
| Monsanto Rheom. 300° F. | | | |
| TS(2) | 17.6 | 14.8 | 18.1 |
| TC(90) | 28.2 | 21.9 | 27.8 |
| Min. Torque | 9.2 | 8.9 | 8.3 |
| Max. Torque | 29.7 | 28.3 | 30.8 |
| % Rebound | | | |
| 73° F. | 43 | 47 | 48 |
| 212° F. | 57 | 61 | 64 |
| MTS 7% def. 10 lb. 10 HZ | | | |
| K'(73° F.) | 960 | 870 | 900 |
| K"(73° F.) | 227 | 173 | 171 |

TABLE XII-continued

| Example/Level (phr) | Control (None) | S (H-47A) | T (H-9) |
|---|---|---|---|
| Tan delta | 0.237 | 0.199 | 0.190 |
| % delta change | Par | −16 | −20 |

The vulcanizable and vulcanized rubber compositions of the invention resulting from the use of the carbon filled rubbers modified with the heterocyclic di-N-oxides in accordance with this invention can be molded or shaped into the desired shapes by known techniques, and they can be used for many purposes for which similar compositions are used. As illustrated above, the vulcanized rubber compositions of the invention exhibit improved mechanical properties such as reduced hysteresis (Tan delta and rebound), and when the rubbers of the invention are utilized in the preparation of tires, the tires are characterized by a reduction in rolling loss and/or running temperature. The entire tire may be constructed of the SBR vulcanizates of the invention or other portions in addition to the treads may be constructed using the vulcanizates of the invention.

In the practice of this invention, the tread can be applied during the building of the green tire in which an uncured, shaped tread of the formulation of the present invention is built onto the carcass following which the green tire is shaped and cured. Alternatively, the tread can be applied to a cured tire carcass from which the previous tread has been buffed or abraded away and the uncured, shaped tread of the present invention cured thereon as a retread.

While the invention has been described and exemplified herein by reference to specific examples, machinery, techniques, procedures and examples, it is understood that it is not restricted to any of these, and numerous variations, combinations and permutations can be made within the scope of the invention as is clear to those skilled in the art.

We claim:

1. A process for preparing filled vulcanizates which comprises
    (A) mixing at a temperature of at least about 140° C., at least one rubber having an unsaturated carbon chain, at least one carbon black and a minor property-improving amount of at least one aromatic heterocyclic di-N-oxide compound of the partial formula

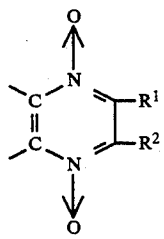
(I)

wherein the depicted carbon atoms are part of an optionally substituted aromatic ring, and $R^1$ and $R^2$ are each independently hydrogen, hydrocarbyl, halohydrocarbyl, hydrocarbyloxy, hydrocarbyl sulfonyl, hydrocarbyl thio, hydrocarbylsulfoxidyl, halogen, amino,

—CN

—OH

—CHO

—CH(O hydrocarbyl)$_2$

—C(O)R$^3$

—C(O)OR$^3$

—C(N—OH)R$^3$

—C(O)NR$^3$R$^6$

—CH=N—NH—C(O)OR$^3$

—CH$_2$OC(O)CH$_3$

—R$^4$YR$^3$

—C(O)NHR$^4$OH

—C(NH)NR$^7$R$^8$, or

—C(I)NHN(R$^3$)$_2$ wherein each $R^3$ is independently hydrogen or a hydrocarbyl group, $R^4$ is a divalent hydrocarbyl group, $R^6$ is hydrogen, hydrocarbyl, —R$^4$OR$^3$, or —R$^4$COOR$^3$; $R^7$ is hydrogen or a hydrocarbyl group; $R^8$ is hydrogen or a hydrocarbyl, an amino, or a hydroxyl group; $R^7$ and $R^8$ may be hydrocarbyl groups joined together to form a ring including the nitrogen atom, and Y is O, divalent S, —NH—, —S(O)— or —S(O)$_2$ or $R^1$ and $R^2$ may be joined together to form a ring including the nitrogen atom, and Y is O or divalent S, or $R^1$ and $R^2$ may be joined together to form further ring systems which may be saturated or unsaturated, and further substituted or unsubstituted, and
    (B) vulcanizing said mixture with a conventional vulcanizing agent which is not a di-N-oxide compound.

2. The process of claim 1 wherein the rubber is NR, IR, BR, SBR, CR, CIIR, NIR or a mixture of two or more of said rubbers.

3. The process of claim 1, wherein the rubber is NR, SBR or a mixture containing at least about 50% of one of these.

4. The process of claim 1 wherein the carbon black has a surface area of at least about 20 m$^2$/g.

5. The process of claim 1 wherein the mixture of (A) is prepared at a temperature of at least about 150° C.

6. The process of claim 1 containing up to about 80 parts by weight of carbon black and up to about 10 parts by weight of the di-N-oxide per 100 parts by weight of rubber.

7. The process of claim 1 wherein $R^1$ is an OH, a CN or a hydrocarbyl group and $R^2$ is hydrogen, a lower hydrocarbyl, lower hydrocarbyloxy or lower hydrocarbylthio group.

8. The process of claim 1 wherein the heterocyclic N-oxide is further characterized by the formula

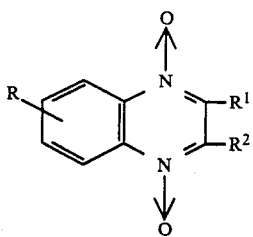

(III)

wherein $R^1$ and $R^2$ are as defined in claim 1 and R is hydrogen, or a hydrocarbyl, hydrocarbyloxy, hydrocarbylthio, hydroxyl, halogen, cyano, amino; —C(O)-hydrocarbyl, amide, or ester group.

9. The process of claim 8 wherein R is hydrogen and $R^1$ and $R^2$ are hydrocarbyl groups.

10. The process of claim 1 wherein the di-N-oxide is further characterized by the formula

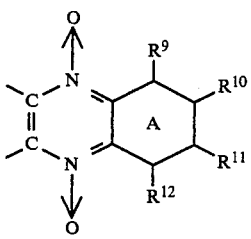

(II)

wherein the depicted carbon atoms are part of an aromatic ring which may be substituted, ring A is aromatic or non-aromatic, $R^9$, $R^{10}$, $R^{11}$ and $R^{12}$ are each independently hydrogen or a hydrocarbyl, hydrocarbyloxy, hydrocarbylthio, hydroxyl, amino, nitro carboxylic, carboxylic ester, amide, or cyano group, and when ring A is an aromatic ring, any two or more adjacent groups may be joined together to form additional aromatic rings.

11. The process of claim 10 wherein ring A is aromatic and at least one of the R groups is a hydroxyl or cyano group.

12. The process of claim 1 wherein the heterocyclic di-N-oxide is further characterized by the formula

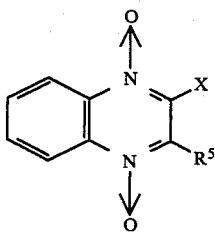

(IV)

wherein X is —OH, —CN, —C(O)OR$^3$, —C(-N—OH)R$^3$, —CHO, —CH(O)—hydrocarbyl)$_2$, —C-(O)NHR$^6$, —C(O)NHN(R$^3$)$_2$, —R$^4$YR$^3$, —C(NH)NR$^7$R$^8$, or —C(O)NHR$^4$OH; R$^5$ is X, hydrogen, a hydrocarbyl, a halohydrocarbyl or hydrocarbyloxy group; R$^3$ is hydrogen or a hydrocarbyl group; R$^4$ is a divalent hydrocarbyl group; R$^6$ is hydrogen, —R$^4$COOR$^3$ or —R$^4$YR$^3$; R$^7$ is hydrogen or a hydrocarbyl group; R$^8$ is hydrogen or a hydrocarbyl, an amino, or a hydroxyl group; or R$^7$ and R$^8$ may be hydrocarbyl groups joined together to form a ring system including the nitrogen atom, and Y is O or divalent S; or X and R$^5$ are hydrocarbyl groups joined together to form further ring systems which are saturated or unsaturated, and further substituted or unsubstituted.

13. The process of claim 12 wherein X is an OH or a CN group and R$^5$ is hydrogen, a lower hydrocarbylthio group.

14. The process of claim 1 wherein the heterocyclic di-N-oxide compound is characterized by the formula

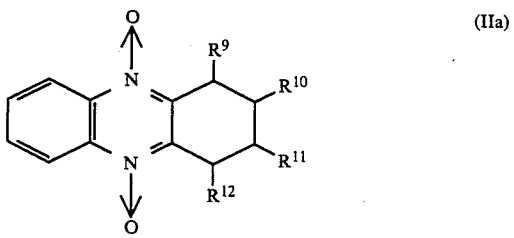

(IIa)

wherein $R^9$, $R^{10}$, $R^{11}$, and $R^{12}$ are each independently hydrogen or lower hydrocarbyl, lower hydrocarbyloxy, hydroxy, or cyano groups and wherein none, one or any two of the aromatic ring positions may be substituted with a hydrocarbyl, hydrocarbyloxy, hydrocarbylthio, hydroxyl, halogen, cyano, amino or —C-(O)—hydrocarbyl groups.

15. The process of claim 14 wherein $R^9$, $R^{10}$, $R^{11}$ and $R^{12}$ are hydrogen atoms.

16. The process of claim 1 wherein the aromatic heterocyclic di-N-oxide compound is characterized further by the formula

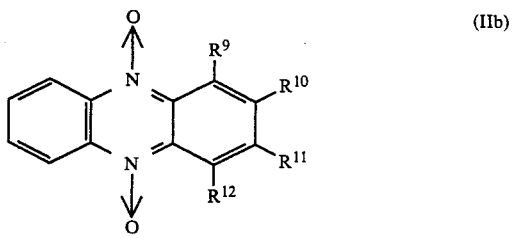

(IIb)

wherein $R^9$, $R^{10}$, $R^{11}$, and $R^{12}$ are each independently hydrogen, or lower hydrocarbyl, lower hydrocarbyloxy, hydroxy or cyano groups, and wherein none, one or any two of the other aromtic ring positions can be substituted with hydrocarbyl, halogen, hydroxyl, hydrocarbyl oxy, hydrocarbyl thio, hydrocarbyl carbonyl, amino, amide, ester or —C(O)—hydrocarbyl groups, and any two or more adjacent R groups may be joined together to form additional aromatic rings.

17. The process of claim 16 wherein $R^9$ and $R^{12}$ are hydrogen, $R^{10}$ is a hydroxyl group, and $R^{11}$ is hydrogen or a hydrocarbyl group.

18. The process of claim 16 wherein the di-N-oxide compound is further represented by the formula

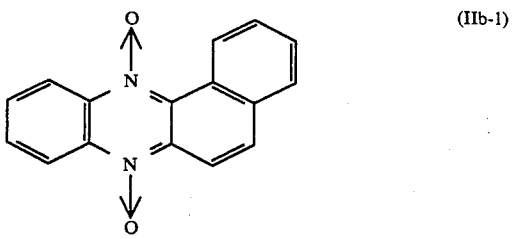

(IIb-1)

wherein none, one, or any of the ring positions can be substituted with hydrocarbyl, hydrocarbyloxy, hydrocarbylthio, halogen, hydroxyl, hydrocarbyl carbonyl, nitro, sulfonyl, carboxyl or amino groups.

19. A process of preparing filled vulcanizates exhibiting reduced hysteresis which comprises the steps of:
(A) mixing at a temperature of at least about 150° C., at least one rubber having an unsaturated carbon chain, at leat one carbon black having a surface area of at least about 20 m²/g, and a property-improving amount of a heterocyclic di-N-oxide compound of the formula

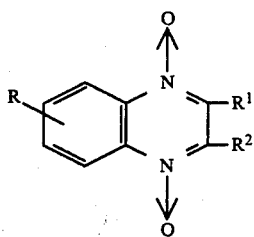

(III)

wherein R¹ and R² are as defined in claim 1, and R is hydrogen, or a hydrocarbyl, hydrocarbyloxy, hydrocarbylthio, hydroxyl, halogen, cyano, amino —C(O) hydrocarbyl, amide or ester group, and (B) vulcanizing said mixture with a conventional vulcanizing agent which is not a di-N-oxide compound.

20. A filled vulcanizate prepared by the process of claim 1.
21. A filled vulcanizate prepared by the process of claim 19.
22. The filled vulcanizate of claim 20 containing up to about 10 parts of the di-N-oxide and up to about 80 parts of carbon black per 100 parts of rubber.
23. The filled vulcanizates of claim 20 wherein the rubber comprises SBR.
24. The filled vulcanizate of claim 21 containing up to about 10 parts of the di-N-oxide and up to about 80 parts of carbon black per 100 parts of rubber.
25. The filled vulcanizate of claim 21 wherein the rubber comprises SBR.
26. A tire characterized by lower rolling loss and having at least the thread portion thereof comprising a filled vulcanizate of claim 20.
27. The tire of claim 26 wherein the stabilizer ply insert, sidewall and/or belt also comprise the filled vulcanizate of claim 20.
28. A tire characterized by lower rolling loss and having at least the tread portion thereof comprising a filled vulcanizate of claim 21.
29. A tire characterized by lower rolling loss and having at least the tread portion thereof comprising a filled vulcanizate of claim 25.

* * * * *